United States Patent
Bunel

(10) Patent No.: US 6,437,192 B1
(45) Date of Patent: Aug. 20, 2002

(54) HYDROFORMYLATION OF CONJUGATED DIENES TO ALKENALS USING PHOSPHONITE LIGANDS

(75) Inventor: Emilio E Bunel, Wilmington, DE (US)

(73) Assignee: E. I. Du Pont de Nmeours and Company, Wilmington, DE (US)

( * ) Notice: Subject to any disclaimer, the term of this patent is extended or adjusted under 35 U.S.C. 154(b) by 0 days.

(21) Appl. No.: 09/715,968

(22) Filed: Nov. 17, 2000

(51) Int. Cl.$^7$ ................................................ C07C 45/50
(52) U.S. Cl. ......................... 568/454; 568/451; 556/14
(58) Field of Search ............................... 568/451, 454; 556/14, 19, 28, 144; 50/155

(56) References Cited

U.S. PATENT DOCUMENTS

| | | |
|---|---|---|
| 3,907,847 A | 9/1975 | Keblys |
| 4,769,498 A | 9/1988 | Billig et al. |
| 5,028,734 A | 7/1991 | Drent |
| 5,210,260 A | 5/1993 | Bohshar et al. |
| 5,250,726 A | 10/1993 | Burke |
| 5,288,903 A | 2/1994 | Bunel et al. |
| 5,312,996 A | 5/1994 | Packett |
| 5,523,453 A | 6/1996 | Breikss |
| 5,710,344 A | 1/1998 | Breikss et al. |
| 5,817,850 A | 10/1998 | Pastor et al. |
| 5,817,883 A | 10/1998 | Briggs et al. |
| 5,821,378 A | 10/1998 | Foo et al. |
| 5,821,389 A | 10/1998 | Briggs et al. |
| 5,886,237 A | 3/1999 | Packett et al. |
| 5,892,127 A | 4/1999 | Packett et al. |

FOREIGN PATENT DOCUMENTS

| | | |
|---|---|---|
| DE | 195 32 394 | 2/1995 |
| EP | 0 033 554 | 8/1981 |
| EP | 0 872 469 | 10/1998 |
| EP | 0 872 483 | 10/1998 |

OTHER PUBLICATIONS

Von Bernhard Fell und Walter Boll, Kobaltcarboynyl– und Rhodiumcarbonyl–Katalysatorsysteme bei der Hydroformylierung von 1,3–Dienen, Chemiker–Zeitung, 99, Jahrgang (1975), Nr. 11, pp. 452–458.

Von Bernhard Fell, Walter Boll und Jens Hagen, Reaktionsprodukte der Hydroformylierung konjugierter Diene mit Rhodiumcarbonyl/tert. Phosphin–Katalysatorsystemen, Chemiker–Zeitung, 99, Jahrgang (1975), Nr. 12, pp. 485–492.

Bernhard Fell and Helmut Bahrmann, The Hydroformylation of Conjugated Dienes, V* Aliphatic Tertiary Phosphines and P–Substituted Phospholanes As Cocatalysts of the Rhodium–Catalysed Hydroformylation of 1.3–Dienes, Journal of Molecular Catalysis, 2 (1977), pp. 211–218.

P.W.N.M. Van Leeuwen and C.F. Roobeek, The Hydroformylation of Butadiene Catalysed By Rhodium–Diphosphine Complexes, Journal of Molecular Catalysis, 31 (1985), pp. 345–353.

Yugi Ohgomori, Naoki Suzuki, Naoko Sumitani, Formation of 1,6–hexanedial via hydroformylation of 1,3–butadiene, Journal of Molecular Catalysis A: Chemical 133 (1998), pp. 289–291.

Bernhard Fell und Peter Hermanns, Hydroformylierung von Buta–1,3–dien und butadienhaltigen Kohlenwasserstofffraktionen nach dem Zweiphasenverfahren, Two–phase Hydroformylation of Buta–1,3–diene and Hydrocarbon Mixtures Containing Buta–1,3–dien, J. prakt. Chem. 340 (1998), pp. 459–467.

(List continued on next page.)

*Primary Examiner*—Sreeni Padmanabhan

(57) ABSTRACT

A hydroformylation process comprising the steps of: (a) reacting a conjugated $C_4$ to $C_{20}$ alkadiene with CO and $H_2$ in the presence of a catalyst composition to form a product comprising at least one alkenal wherein said catalyst composition comprises a Group VIII metal or Group VIII metal compound and at least one phosphonite ligand having a structure:

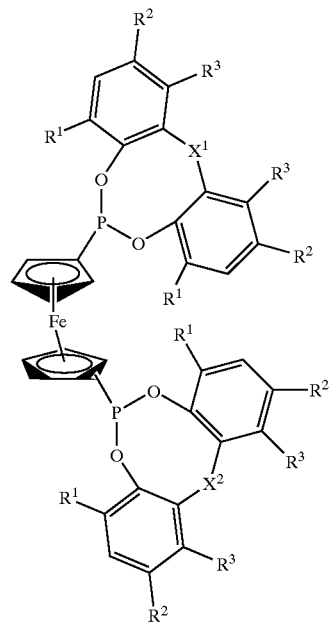

wherein $R^1$, $R^2$ and $R^3$ are independently selected from the group consisting of hydrogen, alkyl of 1 to 20 carbon atoms, aralkyl of 7 to 15 carbon atoms and aryl of 6 to 10 carbon atoms, and wherein $X^1$ and $X^2$ are independently selected from the group consisting of a direct bond and alkylidene of 1 to 20 carbon atoms; and then (a) recovering at least one alkenal. The process is particularly useful to produce pentenals from butadiene.

9 Claims, No Drawings

OTHER PUBLICATIONS

Yoshihiro Sato, Toyoki Nishimata, and Miwako Mori, Novel Synthesis of Heterocycles Using Nickel(O)–Catalyzed [2+2+2] Cocyclization Asymmetric Synthesis of Iosindoline and Isoquinoline Derivatives, Heterocycles, vol. 44, No. 1, 1997, pp. 443–457.

Hiroki Yoshizaki, Hisao Satoh, Yoshihiro Sato, Seiji Nukui, Masakatsu Shibasaki, and Miwako Mori, Palladium–Mediated Asymmetric Synthesis of Cis–3,6–Disubstituted Cyclohexenes. A Short Total Synthesis of Optically Active (+)—Lycorane, J. Org. Chem., 1995, 60, pp. 2016–2021.

Barry M. Trost and Michel Spagnol, Nickel catalysed coupling of allylamines and boronic acids, J. Chem. Soc. Perkin Trans. 1, 1995, pp. 2083–2096.

Manfred T. Reetz, Andreas Gosberg, Richard Goddard and Suk–Hun Kyung, Diphosphonites as highly efficient ligands for enantioselective rhodium–catalyzed hydrogenation, Chem. Commun., 1998, pp. 2077–2078.

J.J. Bishop, A. Davison, M.L. Katcher, D.W. Lichtenberg, R.E. Merrill and J.C. Smart, Symmetrically Disubstituted Ferrocenes, I. The Synthesis of Potential Bidentate Ligands, Journal of Organometallic Chemistry, 27 (1971) pp. 241–249.

Homer R. Yeh, Formation of Sulfoxide 'Dimers' From Hydrogen Peroxide Oxidation of 2–Chloroethyl Methyl Sulfide and 2–Chloroethyl Ethyl Sulfide, Phosphorus, Sulfur, and Silicon, 1992, vol. 68, pp. 1–7.

T. Jongsma, P. Kimkes and G. Challa, A new type of highly active polymer–bound rhodium hydroformylation catalyst, Polymer, 1992, vol. 3, No. 1, pp. 161–165.

R.R. Holmes and J.A. Forstner, Tetraphosphorus Hexamethylhexamide [2,4,6,8,9,10–Hexamethyl–2,4,6,8,9, 10–hexaaza–1,3,5,7–tetraphosphaadamantane; Phosphorus(III) Methylimide] Inorganic Syntheses, vol. 8 (1966), pp. 63–68.

J. Gloede, B. Costisella und H. Gross, Derivatives of o–Phenylene Phosphate.34.Halogenation of o–Methoxyphenyl Phosphinites, Phosphonites, and Phosphites, Z.. anorg. allg. Chem. 535 (1986), pp. 221–228.

O.J. Scherer u. R. Thalacker, Chlorodimethylphosphite–synthesis and some Reactions, Z. Naturforsch, 27b, [1972], pp. 1429–1430.

Gregory D. Cuny and Stephen L. Buchwald, Practical, High–Yield, Regioselective, Rhodium–Catalyzed Hydroformylation of Functionalized a–Olefins, J. Am. Chem. Soc. 1993, 115, pp. 2066–2068.

HYDROFORMYLATION OF CONJUGATED DIENES TO ALKENALS USING PHOSPHONITE LIGANDS

CROSS-REFERENCE TO RELATED APPLICATIONS

"Not Applicable"

STATEMENT REGARDING FEDERALLY SPONSORED RESEARCH OR DEVELOPMENT

"Not Applicable"

BACKGROUND OF THE INVENTION

1. Field of the Invention

This invention relates to the use of certain bisphosphonite ligands in the presence of a Group VIII metal to catalyze the hydroformylation of $C_4$ to $C_{20}$ conjugated dienes to alkenals.

2. Description of the Related Art

The hydroformylation of alkadienes to produce alkenals, for example the hydroformylation of butadiene to pentenals, is generally known. Pentenals are potential intermediates to a variety of useful compounds. Pentenals may be oxidized and optionally esterified to pentenoic acids or methyl pentenoates, which in turn can be hydroformylated to 5-formylvaleric acid or 5-formylvalerates. 5-Formylvaleric acid and 5-formylvalerates are useful intermediates in the production of epsilon caprolactam. Currently processes for the direct production of pentenoic acids or methyl pentenoates by carbonylation of butadiene may require high temperatures; i.e., greater than 120° C. An advantage of hydroformylation of butadiene to pentenals is that it requires much lower temperatures; i.e., less than 100° C.

Most processes to produce pentenoic acid or pentenoate esters involve the use of halide promoted catalysts such as described in U.S. Pat. Nos. 5,250,726 and 5,288,903. These processes have the disadvantage that they use high concentrations of hydrohalogenic acids and other rigorous conditions, which necessitate cost-increasing measures in connection with safety and the corrosion of the equipment. In U.S. Pat. No. 5,028,734 issued Jul. 2, 1991, a process is described for the selective carbonylation of a conjugate diene by contacting with carbon monoxide in the presence of a hydroxyl group-containing compound such as methanol. This catalyst system is less corrosive than the process that is described in U.S. Pat. Nos. 5,250,726 and 5,288,903 but still has the disadvantage of requiring the use of a catalyst consisting of palladium, a bidentate phosphine and an acid to catalyze the transformation of butadiene to pentenoate esters. The main disadvantage of the presence of an acid is its reactivity towards the alcohol and the bidentate phosphines used in the process. Alcohols will react with the acid promoter to produce esters and phosphines will be converted to phosphonium salts. The combination of these two factors renders the invention described in U.S. Pat. No. 5,028,734 non-practical from an industrial point of view.

Pentenals may be alternatively hydrogenated to pentenols, which upon hydroformylation give hydroxyhexanals. 6-Hydroxyhexanal is a useful intermediate in the production of epsilon caprolactone.

Pentenals may be alternatively hydroformylated to dialdehydes, including adipaldehyde. Adipaldehyde is a valuable intermediate which is potentially useful in the production of compounds such as adipic acid (by oxidation), hexamethylenediamine (by reductive amination), and 1,6-hexanediol (by hydrogenation). Production of adipaldehyde by hydroformylation of pentenals would be a desirable improvement over current processes based on the oxidation of cyclohexane because it is based on butadiene, a less expensive feedstock.

Although a variety of complexes of bis(phosphorus) ligands with rhodium catalyze the hydroformylation of butadiene, the selectivity for 3- and 4-pentenals is low for many of them. Various publications in the 1970's and 1980's, describe hydroformylation of butadiene catalyzed by rhodium complexes with monodentate phosphines (For example, Fell, B. and W. Rupilius *Tetrahedron Lett.* 1969, 2721–3; Fell, B. and W. Boll *Chem.-Ztg.* 1975, 99, 452–8; Fell, B., W. Boll, and J. Hagen *Chem.-Ztg.* 1975, 99, 485–92; Fell, B. and H. Bahrmann *J. Mol. Catal.* 1977, 2, 211–18). These systems yield primarily valeraldehyde because the rhodium/phosphine catalysts are also very efficient catalysts for hydrogenation. Van Leeuwen reported that under mild conditions (95° C. and 175 psi (1.3 MPa) 1:1 $H_2$/CO) rhodium complexes of bidentate phosphines also yield primarily valeraldehyde (European Patent No. EP33554 A2, Van Leeuwen, P. W. N. M. and C. F. Roobeek *J. Mol. Catal.* 1985, 31, 345–53). Recently, however, Ohgomori reported that under more vigorous conditions (100° C. and 1300 psi (8.9 MPa) 1:1 $H_2$/CO) these catalysts give 3- and 4-pentenals (Ohgomori, Y., Suzuki, N., and Sumitani, N. *J. Mol. Catal.* 1998, 133, 289–291). However, under these conditions the pentenals undergo further hydroformylation to a mixture of dialdehydes, lowering the yield. It has also been reported that hydroformylation of butadiene under biphasic conditions using the sulfonated phosphine $P(C_6H_4\text{-}3\text{-}SO_3Na)_3$ yields 3-pentenal (B. Fell, P. Hermanns, and H. Bahrmann, *J. Prakt. Chem.*, 340 (1998), pp. 459–467, German Patent No. DE 19532394).

A recent series of patents (U.S. Pat. Nos. 5,312,996, 5,817,883, 5,821,389, European Patent No. 872,469, European Patent No. 872,483, U.S. Pat. Nos. 5,892,127, 5,886,237, and European Patent No. 872,483) discloses a hydroformylation process in which rhodium complexes of bidentate phosphite ligands catalyze the hydroformylation of butadiene to 3-pentenals. U.S. Pat. No. 5,710,344 discloses the use of rhodium complexes of bidentate phosphorus ligands wherein the ligand contains a bridging group bonded through P—O bonds to a pair of trivalent phosphorus atoms with the other two bonds to each phosphorus being either a pair of P—N bonds (phosphorodiaminites), a pair of P—C bonds (phosphinites) or one P—N and one P—C bond (phosphoroaminites).

These prior art processes using rhodium complexes of bidentate phosphorus ligands to produce 3-pentenal from butadiene have various disadvantages. For example, the isolation of 3-pentenal in these systems is complicated by side reactions such as isomerization to 2-pentenal, reduction to valeraldehyde, and further hydroformylation to a mixture of dialdehydes. Thus, these catalysts do not give high selectivity to 3-pentenal at high conversions of butadiene. For example, the highest selectivity reported for a rhodium complex of a bis(phosphite) ligand is 84% at 37% conversion of butadiene (U.S. Pat. No. 5,886,237). The bis (phosphinite) ligands disclosed in U.S. Pat. No. 5,710,344 disclose up to 95% selectivity at 95% conversion of butadiene, but only in the presence of greater than 5 equivalents of the bis(phosphinite) ligand.

Although bidentate phosphonite ligands are not commonly used in catalysis, they have been employed as catalysts for a variety of transformations, including nickel-catalyzed cyclotrimerization of alkynes (*Heterocycles,*

1997, 44, 443–457), nickel- and palladium-catalyzed alkylations and cross couplings (*J. Org. Chem.* 1995. 60, 2016–2; *J. Chem. Soc., Perkin Trans.* 1, 1995, 17, 2083–96), nickel-catalyzed hydrocyanation of olefins (U.S. Pat. No. 5,523,453), and rhodium-catalyzed enantioselective hydrogenation of olefins (Reetz, M., Gosberg, A., Goddard, R., Kyung, S.-H. *Chem. Commun.* 1998, 19, 2077–2078).

Bidentate phosphonite ligands based on a ferrocene backbone have been disclosed in U.S. Pat. No. 5,817,850 and *Chem. Commun.* 1998, 19, 2077–2078. The bidentate phosphonites described in these publications have biphenol or binaphthol derived terminal groups that are bridged. U.S. Pat. No. 5,817,850 claims a hydrocarbonylation reaction of an alkene with carbon monoxide and hydrogen to form an aldehyde which is catalyzed by a transition metal complex of the bridged terminal group containing ferrocene bis(phosphonite) disclosed therein.

BRIEF SUMMARY OF THE INVENTION

In view of the above prior art, the present invention involves the use of catalyst compositions based on certain phosphonite ligands that structurally involve a ferrocene moiety between a pair of phosphorous atoms and a Group VIII metal or Group VIII metal compound in the hydroformylation of alkadienes (i.e., acyclic hydrocarbons with two double bonds) to produce alkenals (i.e., linear ethylenically unsaturated aldehydes).

The invention provides a hydroformylation process comprising the steps of: (a) reacting a conjugated $C_4$ to $C_{20}$ alkadiene with CO and $H_2$ in the presence of a catalyst composition to form a product comprising at least one alkenal wherein said catalyst composition comprises a Group VIII metal or Group VIII metal compound and at least one phosphonite ligand having a structure:

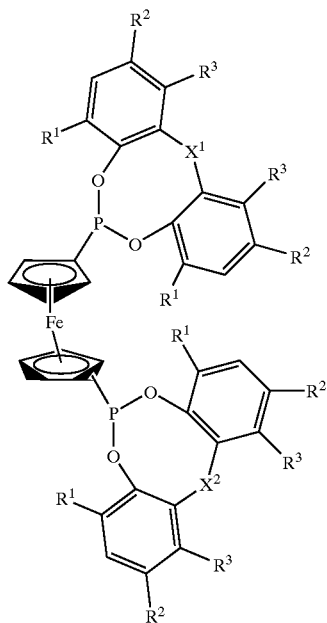

wherein $R^1$, $R^2$ and $R^3$ are independently selected from the group consisting of hydrogen, alkyl of 1 to 20 carbon atoms, aralkyl of 7 to 15 carbon atoms, alkoxy of 1 to 12 carbon atoms and aryl of 6 to 10 carbon atoms, and wherein $X^1$ and $X^2$ are independently selected from the group consisting of a direct bond and alkylidene of 1 to 20 carbon atoms; and then (a) recovering at least one alkenal. It should be appreciated that for purposes of this invention the above structural formula is illustrative of the staggered configuration of bidentate phosphonite ferrocene moiety; i.e., $(\eta^5-C_5H_4PO_2\text{-bridged})_2Fe$, but is not intended to be limiting. As such the eclipsed configuration as generally known in the art as well as rotational variation thereof are to be considered intrinsically equivalent to the illustrated staggered configuration.

The invention is especially directed to a hydroformylation process involving the Group VIII metal or Group VIII metal compound being selected from the group consisting of rhodium, cobalt, iridium, ruthenium, palladium and most preferably the metal being rhodium. Preferably the alkadiene reactant is butadiene and the alkenal products are pentenals.

DETAILED DESCRIPTION OF THE INVENTION

The catalyst compositions usefull in the processes of the invention are comprised of certain bidentate phosphonite ligands and a transition metal.

The phosphonite ligands useful in the hydroformylation process of the present invention may be prepared by a variety of methods known in the art. For example, 1,1'-dilithioferrocene can be prepared according to *J. Organomet. Chem.*, 1971, 27(2), 241–9. 1,1'-Bis(dichlorophosphino)ferrocene can be prepared from the 1,1'-dilithioferrocene according to *Phosphorus, Sulfur Silicon Relat. Elem.*, 1992, 68(1–4), 99–106 or *Chem. Commun.* (Cambridge), 1998, 19, 2077–2078. The desired phosphonite ligands useful in the process according to the instant invention can be prepared by contacting 1,1'-bis(dichlorophosphino)ferrocene with two or more equivalents of a substituted or unsubstituted bridged biphenol. *Chem. Commun.* (Cambridge), 1998, 19, 2077–2078 describes the related reaction of 1,1'-bis(dichlorophosphino)-ferrocene with (R)-binaphthol at temperatures greater than 25° C. We have found, however, that in the presence of a base such as triethylamine, this reaction can be carried out at room temperature.

Alternatively, the phosphonite ligands may be prepared by contacting 1,1'-dilithioferrocene (preferably complexed with other labile ligands) with two or more equivalents of a substituted or unsubstituted bridged phosphorochlorodite of the following structure:

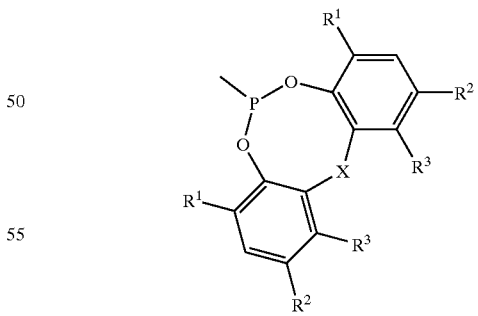

wherein again $R^1$, $R^2$ and $R^3$ are independently selected from the group consisting of hydrogen, alkyl of 1 to 20 carbon atoms, aralkyl of 7 to 15 carbon atoms and aryl of 6 to 10 carbon atoms, and wherein X is selected from the group consisting of a direct bond and alkylidene of 1 to 20 carbon atoms.

Phosphorochloridites may be prepared by a variety of methods known in the art, for example, see descriptions in Polymer, 1992, 33, 161; Inorganic Synthesis, 1966, 8, 68; U.S. Pat. No. 5,210,260; Z. Anorg. Allg. Chem., 1986, 535, 221. With ortho-substituted phenols, phosphorochloridites can be prepared in situ from $PCl_3$ and the phenol. Also, phosphorochloridites of 1-naphthols can be prepared in situ from $PCl_3$ and 1-naphthols in the presence of a base like triethylamine. Another process for preparing the phosphorochloridite comprises treatment of N,N-dialkyl diarylphosphoramidite with HCl. $ClP(OMe)_2$ has been prepared in this manner, see Z. Naturforsch, 1972, 27B, 1429. Phosphorochloridites derived from substituted phenols have been prepared using this procedure as described in commonly assigned U.S. Pat. No. 5,821,378. By contacting the thus obtained phosphorochloridite with 1,1'-dilithioferrocene, for example by the method described in U.S. Pat. No. 5,817,850, a bidentate phosphonite ligand useful according to the invention is obtained.

The transition metal may be any transition metal capable of carrying out catalytic transformations and may additionally contain labile ligands which are either displaced during the catalytic reaction, or take an active part in the catalytic transformation. Any of the transition metals may be considered in this regard. The preferred metals are those comprising Group VIII of the Periodic Table. The preferred metals for hydroformylation are rhodium, cobalt, iridium, ruthenium, palladium and platinum, and rhodium is especially preferred.

Group VIII compounds suitable for hydroformylation, can be prepared or generated according to techniques well known in the art, as described, for example, WO 95 30680, U.S. Pat. No. 3,907,847, and J. Amer. Chem. Soc., 1993,115, 2066. Examples of suitable Group VIII metals are ruthenium, rhodium, and iridium. Suitable Group VIII metal compounds are hydrides, halides, organic acid salts, acetylacetonates, inorganic acid salts, oxides, carbonyl compounds and amine compounds of these metals. Examples of suitable Group VIII metal compounds are, for example, $Ru_3(CO)_{12}$, $Ru(NO_3)_2$, $RuCl_3(Ph_3P)_3$, $Ru(acac)_3$, $Ir_4(CO)_{12}$, $IrSO_4$, $RhCl_3$, $Rh(NO_3)_3$, $Rh(OAc)_3$, $Rh_2O_3$, $Rh(acac)(CO)_2$, $[Rh(OAc)(COD)]_2$, $Rh_4(CO)_{12}$, $Rh_6(CO)_{16}$, $RhH(CO)(Ph_3P)_3$, $[Rh(OAc)(CO)_2]_2$, and $[RhCl(COD)]_2$ (wherein "acac" is an acetylacetonate group; "OAc" is an acetyl group; "COD" is 1,5-cyclooctadiene; and "Ph" is a phenyl group). However, it should be noted that the Group VIII metal compounds are not necessarily limited to the above listed compounds. The Group VIII metal is preferably rhodium. Rhodium compounds that contain ligands that can be displaced by the multidentate phosphites are a preferred source of rhodium. Examples of such preferred rhodium compounds are $Rh(CO)_2$ (acetylacetonate), $Rh(CO)_2(C_4H_9COCHCO-tC_4H_9)$, $Rh_2O_3$, $Rh_4(CO)_{12}$, $Rh_6(CO)_{16}$, $Rh(O_2CCH_3)_2$, and Rh(2-ethylhexanoate). Rhodium supported on carbon may also be used in this respect; i.e., as the source of rhodium.

The hydroformylation process of the present invention provides for reacting an unsaturated diene compound with a source of CO and $H_2$ in the presence of a catalyst composition comprising a Group VIII transition metal preferably selected from the group consisting of Co, Rh, Ru, Ir, Pd, and Pt, and at least one bidentate phosphonite ligand represented by structural formula as described above. The unsaturated starting materials (i.e., the alkadiene) useful in this invention to produce the desired alkenal include generally any unsaturated organic compound containing at least two carbon to carbon double bond, "C=C", and preferably from 4 to 20 carbon atoms. As such, the use of the term alkadiene includes both branched and unbranched $C_4$ to $C_{20}$ compounds with at least two carbon to carbon double bonds which may or may not be terminal double bonds. Examples of suitable diene unsaturated starting material also include, for example, 1,3-butadiene, 1,5-hexadiene, 1,7-octadiene, and norbornadiene; mixtures of octadienes prepared by dimerization of butadiene; cycloaliphatic dienes such as cyclohexadiene, cyclooctadiene, and cycloundecadiene; oligomeric isomer mixtures derived from an olefin and a diene such as a dimer to tetramer mixtue of butadiene and a olefin including propylene, n-butene, isobutene or the like; and mixtures of the same. Also, the unsaturated diene starting compounds can be substituted with one or more functional groups containing a heteroatom, such as oxygen, sulfur, nitrogen, or phosphorus.

The invention is especially directed to hydroformylation processes in which a linear olefinically unsaturated aldehyde is prepared starting from a conjugated diene. The hydroformylation of $C_4$ to $C_{20}$ conjugated dienes to alkenals is especially preferred, for example, the hydroformylation of butadiene to pentenal.

It is a significant advantage of the invention that concentration of the unsaturated starting materials in the reactor may be increased. The normal undesirable side effects of such an increase, for example, the formation of oligomer and/or the inhibition of the catalyst, are avoided. Solvent recycle may be reduced or eliminated with its attendant benefits. In one preferred embodiment of the invention, the concentrations of the unsaturated starting materials may be at least as high as 40 weight percent.

The hydroformylation process according to the invention can be performed as described below:

The reaction conditions of the hydroformylation process according to this invention are in general the same as used in a conventional process, described, for example, in U.S. Pat. No. 4,769,498, which is incorporated herein by reference, and will be dependent on the particular starting unsaturated organic compound. For example, the temperature can be from room temperature to 200° C., preferably from 50 to 120° C. The pressure may vary from atmospheric pressure to 20 MPa, preferably from 3 to 20 MPa for conjugated dienes such as 1,3-butadiene. The pressure is, as a rule, equal to the combined hydrogen and carbon monoxide partial pressure. Extra inert gases may however be present. The molar ratio of hydrogen to carbon monoxide is generally between 10 to 1 and 1 to 10, preferably between 6 to 1 and most preferably 1 to 2.

The amount of Group VIII metal compound is not specially limited, but is optionally selected so that favorable results can be obtained with respect to catalyst activity and economy. In general, the concentration of Group VIII metal in the reaction media is between 10 and 10,000 ppm and more preferably between 50 and 500 ppm, calculated as the free metal.

The molar ratio of multidentate phosphorus ligand to Group VIII metal is not specially limited, but is optionally selected so that favorable results can be obtained with respect to catalyst activity, aldehyde selectivity, and process economy. This ratio generally is from about 0.5 to 100 and preferably from 1 to 5 (moles of ligand to moles of metal). It should be further appreciated that ligands other than those described in the previous structural formula for the ferrocene bisphosphonites of the instant invention may be present provided their presence is not detrimental to the catalyst, reactant and/or product The choice of solvent is not critical again provided the solvent is not detrimental to catalyst, reactant and/or product. The solvent may be a mixture of reactants, such as the starting unsaturated compound, the aldehyde product and/or by-products. Suitable solvents include saturated hydrocarbons such as kerosene, mineral oil or cyclohexane, ethers such as diphenyl ether, tetrahydrofuran or a polyglycol, ketones such as methyl ethyl ketone and cyclohexanone, nitrites such as acetonitrile, valeronitrile, and benzonitrile, aromatics such as toluene, benzene and xylene, esters such as dimethylformamide, and sulfones such as tetramethylenesulfone.

The following examples are presented to more fully demonstrate and further illustrate various individual aspects and features of the present invention and the showings are intended to further illustrate the differences and advantages of the present invention. As such, the examples are felt to be non-limiting and are meant to illustrate the invention but are not meant to be unduly limiting.

EXAMPLE

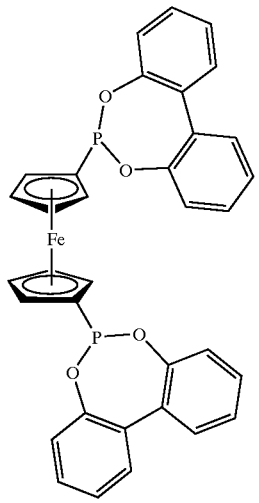

Ligand 1

All manipulations were carried out in a drybox under an atmosphere of nitrogen. To a cold (−30° C.) solution of 2,2'-biphenol phosphorochloridite (14 g, 56 mmol) in toluene (100 mL) was added a cold (−35° C.) suspension of the tetramethylethylenediamine (TMEDA) complex of dilithioferrocene (6 g, 14 mmol) in toluene (70 mL). After the addition was complete, the reaction was allowed to warm to room temperature and stirred at 25° C. for 18 hours. The solution was filtered through neutral alumina, and the solvent was removed to give 3 grams of an orange solid. $^{31}$P NMR (d$_8$-toluene): δ163 ppm.

EXAMPLE 1A
Hydroformylation of Butadiene Using Ligand 1

A solution containing Rh(acac)(CO)$_2$ (0.057 g), Ligand 1 (0.149 g), butadiene (6.30 g) and 1,2-dichlorobenzene (1.89 g, GC internal standard) in 49 grams of toluene was prepared in a drybox. This solution was loaded into a 100 mL autoclave under a stream of H$_2$/CO. The autoclave was charged to 100 psig (0.69 MPa) with 1:1 H$_2$/CO and heated to 95° C. Once the temperature had stabilized, the pressure was adjusted to 950 psig (6.6 MPa). The mixture was stirred at approximately 900 rpm with an air-driven rotary stirrer for 240 minutes. Samples were withdrawn via needle valve and analyzed by gas chromatography on a Hewlett Packard (Palo Alto, Calif.) 5890A Chromatograph with a fused silica capillary column (Model DB5, 30 meters, 0.32 mm I.D., 0.25 μm film thickness) purchased from J&W Scientific (Folsom, Calif.). GC analysis after 150 minutes indicated conversion of butadiene: 32.8%; selectivity to 3- and 4-pentenals: 76.4% on a mole basis.

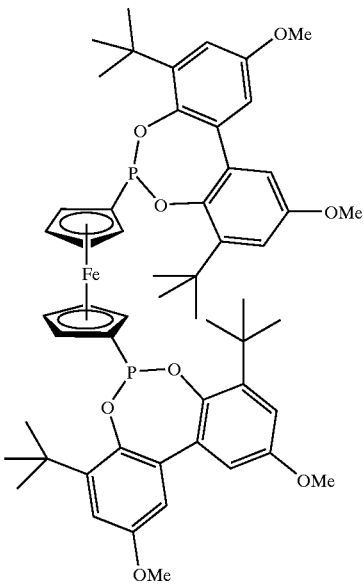

Ligand 2

All manipulations were carried out in a drybox under an atmosphere of nitrogen. To a cold (−30° C.) solution of 4,-4'-dimethoxy-3,3'-ditertbutyl-2,2'-biphenol phosphorochloridite (4.6 g, 10.8 mmol) in tetrahydrofuran (50 mL) was added a cold (−35° C.) suspension of the TMEDA complex of dilithioferrocene (1.57 g, 3.6 mmol) in toluene (40 mL). After the addition was complete, the reaction was allowed to warm to room temperature and stirred at 25° C. for 48 hours. The solution was filtered through neutral alumina, and the solvent was removed. The residue was dissolved in toluene and pentane was added to precipitate Ligand 2 as a yellow crystalline solid (3.5 g). $^{31}$P NMR (d$_8$-toluene): δ164 ppm.

Example 2A
Hydroformylation of Butadiene Using Ligand 2

A solution containing Rh(acac)(CO)$_2$ (0.080 g), Ligand 2 (0.802 g), butadiene (9.02 g) and 1,2-dichlorobenzene (2.0 g, GC internal standard) in 70 grams of toluene was prepared in a drybox. This solution was loaded into a 100 mL autoclave under a stream of H$_2$/CO. The autoclave was charged to 65 psig (4.5 MPa) with 1:1 H$_2$/CO and heated to 95° C. Once the temperature had stabilized, the pressure was adjusted to 900 psig (6.2 MPa). The mixture was stirred at approximately 900 rpm with an air-driven rotary stirrer for 240 minutes. Samples were withdrawn via needle valve and analyzed by gas chromatography on a Hewlett Packard (Palo Alto, Calif.) 5890A Chromatograph with a fused silica capillary column (Model DB5, 30 meters, 0.32 mm I.D., 0.25 μm film thickness) purchased from J&W Scientific (Folsom, Calif.). GC analysis after 90 minutes indicated conversion of butadiene: 71%; selectivity to 3- and 4-pentenals: 85% on a mole basis.

Having thus described and exemplified the invention with a certain degree of particularity, it should be appreciated that the following claims are not to be so limited but are to be afforded a scope commensurate with the wording of each element of the claim and equivalents thereof.

I claim:

1. A hydroformylation process comprising the steps of:
   (a) reacting a conjugated $C_4$ to $C_{20}$ alkadiene with CO and $H_2$ in the presence of a catalyst composition to form a product comprising at least one alkenal wherein said catalyst composition comprises a Group VIII metal or Group VIII metal compound and at least one phosphonite ligand having a structure:

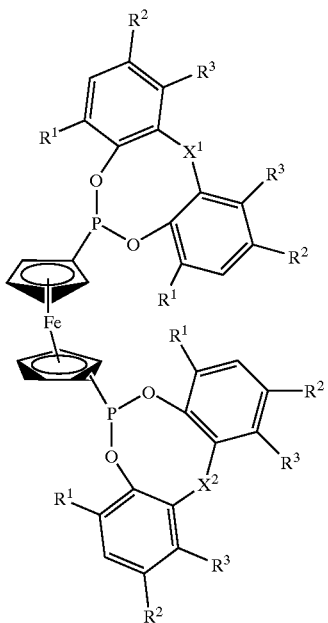

wherein $R^1$, $R^2$ and $R^3$ are independently selected from the group consisting of hydrogen, alkyl of 1 to 20 carbon atoms, aralkyl of 7 to 15 carbon atoms, alkoxy of 1 to 12 carbon atoms, and aryl of 6 to 10 carbon atoms, and wherein $X^1$ and $X^2$ are independently selected from the group consisting of a direct bond and alkylidene of 1 to 20 carbon atoms; and
   (a) recovering at least one alkenal.

2. The process according to claim 1 wherein the metal of said Group VIII metal or Group VIII metal compound is selected from the group consisting of rhodium, cobalt, iridium, ruthenium, palladium and platinum.

3. The process of claim 2 wherein the metal is rhodium.

4. The process of claim 1 wherein the catalyst composition or alkadiene is in the liquid phase.

5. The process of claim 1 wherein the alkadiene is butadiene and the alkenal is pentenal.

6. The process of claim 1 wherein the conversion of butadiene is at least 70 percent.

7. The process of claim 1 wherein the selectivity to alkenal is at least 75 percent.

8. The process of claim 1 wherein the phosphonite ligand is:

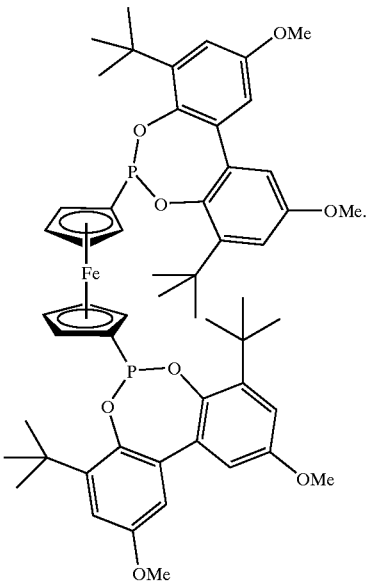

9. The process of claim 1 wherein the phosphonite ligand is:

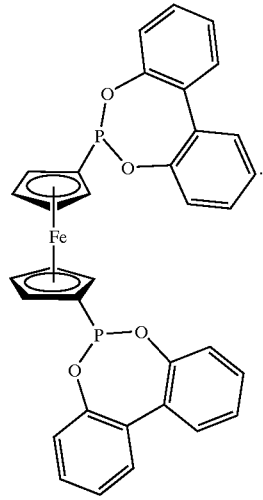

* * * * *

UNITED STATES PATENT AND TRADEMARK OFFICE
CERTIFICATE OF CORRECTION

PATENT NO.    : 6,437,192 B1
DATED         : August 20, 2002
INVENTOR(S)   : Emilio E. Bunel It is certified that error appears in the above-identified patent and that said Letters Patent is hereby corrected as shown below:

<u>Column 9,</u>
Line 55, delete the number "6" and insert the number -- 5 --.

Signed and Sealed this

Eleventh Day of February, 2003

JAMES E. ROGAN
*Director of the United States Patent and Trademark Office*